US012805941B2

(12) United States Patent
Roche

(10) Patent No.: US 12,805,941 B2
(45) Date of Patent: Nov. 24, 2026

(54) INTRA-OPERATIVE AND POST-OPERATIVE POSITION, MOTION, AND ORIENTATION SYSTEM

(71) Applicant: Martin Roche, Fort Lauderdale, FL (US)

(72) Inventor: Martin Roche, Fort Lauderdale, FL (US)

( * ) Notice: Subject to any disclaimer, the term of this patent is extended or adjusted under 35 U.S.C. 154(b) by 982 days.

(21) Appl. No.: 17/646,566

(22) Filed: Dec. 30, 2021

(65) Prior Publication Data

US 2022/0202505 A1 Jun. 30, 2022

Related U.S. Application Data

(60) Provisional application No. 63/132,738, filed on Dec. 31, 2020.

(51) Int. Cl.

*A61B 34/20* (2016.01)
*A61B 5/00* (2006.01)
*A61B 5/11* (2006.01)
*A61B 17/90* (2006.01)

(52) U.S. Cl.

CPC ................ *A61B 34/20* (2016.02); *A61B 5/11* (2013.01); *A61B 5/48* (2013.01); *A61B 5/6878* (2013.01); *A61B 5/688* (2013.01); *A61B 5/6882* (2013.01); *A61B 17/90* (2021.08); *A61B 2562/0219* (2013.01)

(58) Field of Classification Search

CPC . A61B 17/16; A61B 34/20; A61B 2034/2046; A61B 2034/2048

See application file for complete search history.

(56) References Cited

U.S. PATENT DOCUMENTS

| | | | | |
|---|---|---|---|---|
| 8,372,147 | B2 * | 2/2013 | Roche | A61B 5/4533 623/17.11 |
| 8,372,153 | B2 * | 2/2013 | Roche | A61B 5/1459 623/20.14 |
| 9,192,392 | B2 * | 11/2015 | van der Walt | A61B 17/1764 |
| 9,549,742 | B2 * | 1/2017 | Berend | A61F 2/4684 |
| 10,117,748 | B2 * | 11/2018 | Fanson | A61B 90/39 |
| 10,499,997 | B2 * | 12/2019 | Weinstein | A61B 90/361 |
| 10,716,580 | B2 * | 7/2020 | Berend | A61B 17/157 |

(Continued)

*Primary Examiner* — Anu Ramana

(74) *Attorney, Agent, or Firm* — Bookoff McAndrews, PLLC

(57) ABSTRACT

A surgical system for intra-operative and post-operative measurement of motion and position of the musculoskeletal system. The surgical system comprises a surgical navigation system configured to support the installation of at least one prosthetic component. The surgical navigation system measures motion and position of the musculoskeletal system during surgery. Holes are drilled in a first bone and a second bone of the musculoskeletal system to retain tracking devices of the surgical navigation system. Leaving the holes in the first bone and the second bone after completing the surgery can introduce stress risers that could reduce bone integrity. The surgical system includes a first implantable device and a second implantable device each having anchors corresponding to the holes of the first bone and the second bone. The first implantable device and the second implantable device each has an IMU to measure motion and position post-operatively. The anchors are configured to reduce stress risers.

21 Claims, 6 Drawing Sheets

(56) References Cited

U.S. PATENT DOCUMENTS

| | | | | |
|---|---|---|---|---|
| 10,918,499 | B2 * | 2/2021 | Nielsen | A61B 34/20 |
| 11,020,245 | B2 * | 6/2021 | van der Walt | A61B 34/20 |
| 11,071,456 | B2 * | 7/2021 | Hunter | A61F 2/16 |
| 11,191,594 | B2 * | 12/2021 | Morgan | A61B 17/88 |
| 11,375,975 | B2 * | 7/2022 | Behzadi | A61F 2/4609 |
| 11,484,368 | B2 * | 11/2022 | Krebs | A61B 90/361 |
| 11,596,479 | B2 * | 3/2023 | McGuan | G06N 5/01 |
| 11,660,148 | B2 * | 5/2023 | Walen | A61B 34/76<br>606/87 |
| 11,707,224 | B2 * | 7/2023 | Trabish | A61B 5/6812<br>600/595 |
| 11,707,330 | B2 * | 7/2023 | Weinstein | A61B 34/20<br>606/86 R |
| 11,931,267 | B2 * | 3/2024 | Wilde | A61F 2/4603 |
| 11,998,349 | B2 * | 6/2024 | Hunter | A61B 5/4851 |
| 12,138,181 | B2 * | 11/2024 | Gross | H04W 84/18 |
| 12,178,522 | B2 * | 12/2024 | Morgan | A61B 34/20 |
| 12,285,234 | B2 * | 4/2025 | Hunter | A61B 5/4851 |
| 2010/0100011 | A1 * | 4/2010 | Roche | A61B 5/4528<br>623/20.14 |
| 2013/0218272 | A1 | 8/2013 | Clifford et al. | |
| 2017/0202660 | A1 | 7/2017 | Baird et al. | |
| 2018/0098774 | A1 | 4/2018 | Bonutti | |
| 2020/0163721 | A1 * | 5/2020 | Aghazadeh | A61F 2/34 |
| 2020/0281471 | A1 | 9/2020 | Hunter et al. | |
| 2020/0282108 | A1 | 9/2020 | Wilson et al. | |
| 2021/0330385 | A1 | 10/2021 | Robichaud et al. | |
| 2021/0353431 | A1 * | 11/2021 | Wilde | A61B 34/20 |
| 2022/0296390 | A1 * | 9/2022 | Paszicsnyek | A61F 2/4609 |
| 2024/0358322 | A1 * | 10/2024 | Hunter | A61B 5/4851 |

* cited by examiner

INTRA-OPERATIVE AND POST-OPERATIVE POSITION, MOTION, AND ORIENTATION SYSTEM

FIELD

The present invention pertains generally to medical devices, and particularly to, but not exclusively to, a medical system for generating measurement data or to provide therapy.

BACKGROUND

The musculoskeletal system of a mammal is subject to variations among species. Further changes can occur due to environmental factors, degradation through use, and aging. A joint of the musculoskeletal system typically comprises two or more bones that move in relation to one another. Movement is enabled by muscle tissue and tendons that is a part of the musculoskeletal system. Ligaments can position, hold, and stabilize one or more bones of a joint. Cartilage is a wear surface that prevents bone-to-bone contact, distributes load, and lowers friction.

There has been substantial growth in the repair of the human musculoskeletal system. In general, prosthetic joints have evolved using information from simulations, mechanical prototypes, and patient data that is collected and used to initiate improved designs. Similarly, the tools being used for orthopedic surgery have been refined over the years but have not changed substantially. Thus, the basic procedure for correction of the musculoskeletal system has been standardized to meet the general needs of a wide distribution of the population. Although the tools, procedure, and artificial replacement systems meet a general need, each replacement procedure is subject to significant variation from patient to patient. The correction of these individual variations relies on the skill of the surgeon to adapt and fit the replacement joint using the available tools to the specific circumstance. It would be of great benefit if a system could be developed that improves surgical outcomes and reduces the cost and time of a surgery.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
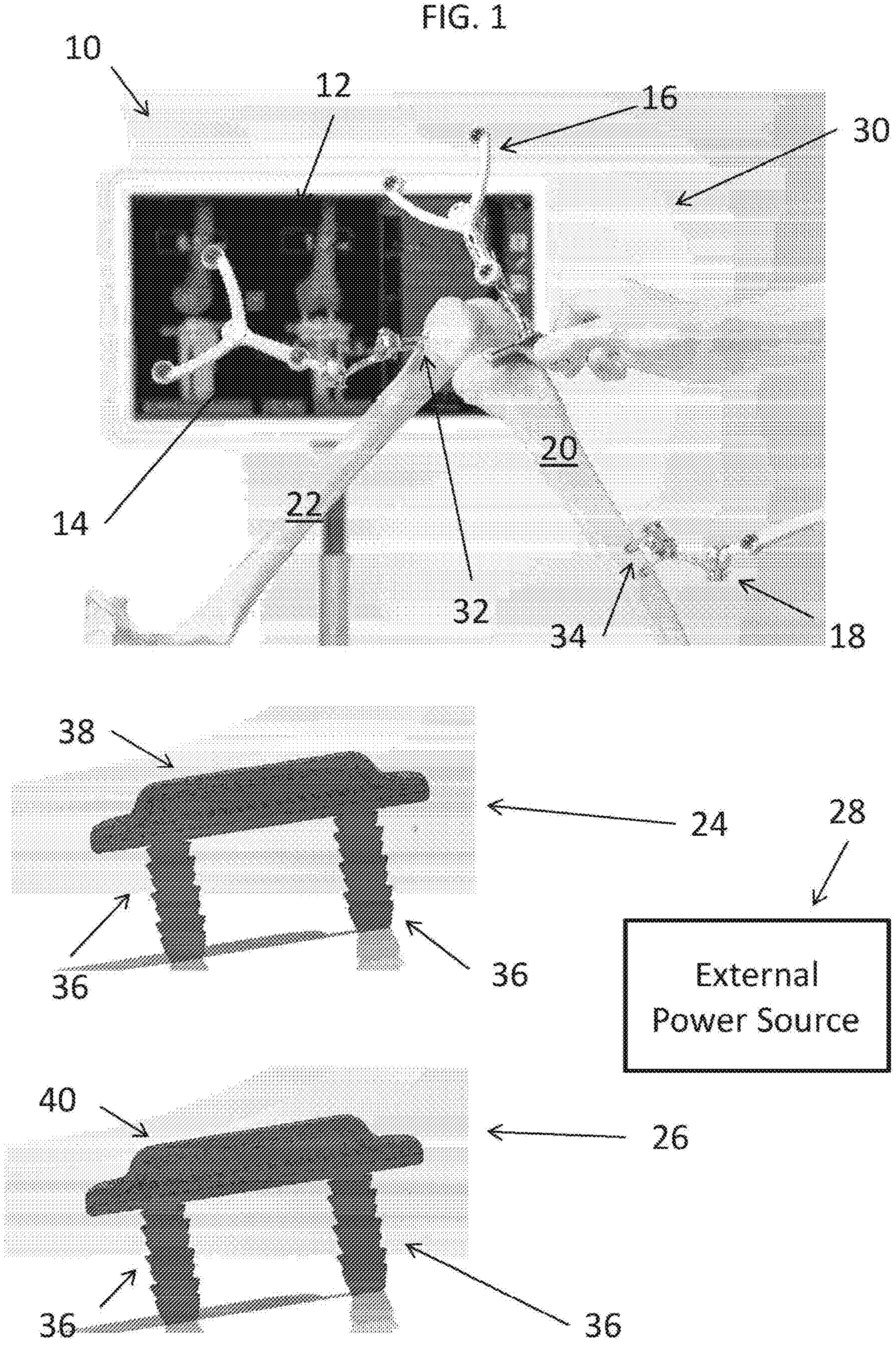
FIG. 1 is an illustration of a surgical system in accordance with an example embodiment.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the device are illustrative only and do not limit use for other parts of a body or for other applications. The device is used to measure at least parameter to generate quantitative measurement data. The devices disclosed herein below are configured to support health, healing, and generate quantitative measurement data related to the human body. In one embodiment, the devices are configured to couple to a musculoskeletal system and can be used on or in the knee, hip, ankle, spine, shoulder, hand, wrist, foot, fingers, toes, bone, muscle, ligaments, tendons and other areas of the musculoskeletal system. Although one or more examples may describe uses in regards to the musculoskeletal system the principles disclosed herein are meant to be adapted for use to all locations on or within the human body. The following description of embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation of the X, Y, Z axes of rectangular Cartesian coordinates is selected to facilitate graphical display on computer screens having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, or MEMs devices) can be used within the scope of the embodiments described.

At least one embodiment is directed to a kinetic orthopedic measurement system that is configured to measure motion and position. The measurement system can be used in surgery to determine real time alignment, range of motion, loading, impingement, and contact point of orthopedic implants. Although the system is generic to any orthopedic assessment, pre-operative measurement, surgery, rehabilitation, or long-term monitoring (e.g., spinal, shoulder, knee, hip, ankle, wrist, finger, toe, bone, musculoskeletal, etc.) the following examples deal with the use in the orthopedic field as a non-limiting example of an embodiment of the invention.

The non-limiting embodiment described herein is related to quantitative measurement used for orthopedic assessment and referred to herein as the kinetic system. The kinetic system includes a sensor system that provides quantitative measurement data and feedback that can be provided visually, audibly, or haptically to a patient, doctor, medical staff, therapist, surgeon or surgical team. The kinetic system provides real-time dynamic data regarding sensor information and position information related to the musculoskeletal system.

In general, kinetics is the study of the effect of forces upon the motion of a body or system of bodies. Disclosed herein is a system for kinetic assessment of the musculoskeletal system. The kinetic system can be for monitoring and assessment of the musculoskeletal system or installed prosthetic components coupled to the musculoskeletal system. For example, installation of a prosthetic component can require one or more bone surfaces to be prepared to receive a device or component. The kinetic system is designed to take quantitative measurements related to movement of one or more bones of the musculoskeletal system, take measurements from one or more sensors to monitor health, or provide therapy to support healing. The sensors are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled. In one embodiment, one or more devices can be coupled to one or more bones of the musculoskeletal system. In one embodiment the one or more devices can measure position, movement, acceleration, and relative motion. In one embodiment, one or more implantable devices can be implanted in one or more bones to provide measurement data. Alternatively, one or more sensors can be coupled to the skin as a flexible patch. In one embodiment, the implantable devices can be in communication with the implantable devices as a system working together to in a specific application.

A prosthetic joint installation can benefit from quantitative measurement data in conjunction with subjective feedback of the prosthetic joint to the surgeon. Pre-operative measurement data can be collected to provide a patient pathology and set expectations and outcomes from a surgical or prosthetic component solution. The quantitative measurements can be used to determine adjustments to bone, prosthetic components, or tissue prior to final installation. Permanent sensors can also be housed in final prosthetic components to provide periodic data related to the status of the implant. Alternatively one or more devices can be coupled to bone during surgery to install the prosthetic component or prosthetic joint. The one or more devices act independently from the prosthetic component or prosthetic joint. Data collected intra-operatively and long term can be used to determine parameter ranges for surgical installation and to improve future prosthetic components. One or more sensors used post-operatively can be used to monitor motion of the musculoskeletal system to determine how the repair is performing and provide feedback based on quantitative measurement data. The physical parameter or parameters of interest can include, but are not limited to, measurement of alignment, load, force, pressure, position, displacement, density, viscosity, pH, spurious accelerations, color, movement, chemical composition, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, equipment, or other physical system.

At least one embodiment is directed to a system for adjusting or monitoring position of the musculoskeletal system for stability, alignment, balance, and range of motion. Examples of monitoring can comprise: a prosthetic component configured to rotate after being coupled to a bone; a sensored prosthesis having an articular surface where the sensored prosthesis is configured to couple to a second prosthetic component, the sensored prosthesis has a plurality of load sensors coupled to the articular surface and a position measurement system configured to measure position, slope, rotation, or trajectory, a remote system configured to wirelessly receive quantitative measurement data from the sensored prosthesis where the remote system is configured to display the articular surface, where the remote system is configured to display position of applied load to the articular surface, and where the remote system is configured to report impingement as the musculoskeletal joint is moved through a range of motion (ROM).

Embodiments of the invention are broadly directed to measurement of physical parameters. Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, temperatures, times, energies etc. . . . for process steps or specific structure implementations should be interpreted to be illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention these parameters are measured with an integrated wireless sensing module or device comprising an i) encapsulating structure that supports sensors and contacting surfaces and ii) an electronic assemblage that integrates a power supply, sensing elements, ultrasound resonator or resonators or transducer or transducers, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

An implanted device can incorporate microelectronic integration into a navigation system. There is a need for appropriate tunnel placement in the tibia or femur to support healing and post-operative function. Problems can occur if the graft is placed inappropriately causing impingement, pain limited range of motion, and graft failure. In one embodiment, the surgeon can place the implanted device in the intra-articular non-loaded area of the femur and one in the tibia. The navigation system registers the fiducials relative to the femoral and tibial bone model of the patient. A pre-operative MRI can be utilized or an intra-operative ultra-scan to register femur and tibia to the navigation system. In the example, the implanted device will have IMU (inertial measurement unit) electronics that can be registered or related to a bone through a registration process. The implanted device can include one or more MEMs (micro-electro-mechanical systems) devices, a camera, or video device. In the example, measurement data from the implanted device can be transmitted to a computer having a display to provide the measurement data in real-time.

FIG. 1 is an illustration of a surgical system 10 in accordance with an example embodiment. Surgical system 10 is configured to intra-operatively and post-operatively monitor movement of the musculoskeletal system. Surgical system 10 comprises a surgical navigation system 30, an implant device 24, and an implant device 26. The surgical system 30 includes a computer 12 having a display that is in view of the surgeon or surgical team to review measurement data in real-time. Surgical system 10 includes one or more implant devices configured to monitor movement of the musculoskeletal system post-operatively. Surgical system 10 improves quality of orthopedic surgery by reducing alignment errors, support implant placement, improve musculoskeletal performance, and improve implant reliability. Surgical system 10 can be configured to measure alignment, rotation, range of motion in support of an installation of a prosthetic component. Surgical navigation system 30 can be an image based, non-image based, ultrasonic, infrared, or other measurement methodology. Surgical navigation system can be used in conjunction with pre-operative scans of the musculoskeletal system or fluoroscopy to support implant positioning. In general, surgical system 10 can be used for a variety of functions such as fracture repair, ligament reconstruction, repair angular deformities, tumor resection, joint arthroplasty, and verification of implant placement.

Surgical navigation system 30 is configured to couple to one or more bones in the musculoskeletal system. In the example, surgical system 10 is coupled to a tibia 20 and a femur 22. A tracking device 14 is coupled to tibia 22. A tracking device 18 is coupled to femur 20. Also shown is a tracking device 16 to support one or more bone cuts that can be aligned by navigation to cut tibia 20 or femur 22 for respectively receiving a tibial prosthetic component and a femoral prosthetic component. Tracking device 14 and tracking device 18 are typically located to allow the surgeon access to the knee joint to install the prosthetic knee joint. Although the example disclosed relates to the knee joint, the concepts disclosed herein can be adapted for use to any part of the musculoskeletal system such as hip, shoulder, elbow, ankle, spine, hand, wrist, toes, or bone. In one embodiment, one or more holes are drilled in tibia 20 and femur 22 for mounting tracking device 18 and tracking device 14. The one or more holes are drilled in areas of tibia 20 or femur 22 having sufficient bone mass to support drilling and retaining tracking devices 14 or 18. In one embodiment, the one or more holes drilled in tibia 20 or femur 22 can be accessed for drilling using the wound opened for the installation of the one or more prosthetic components. This minimizes the risk of infection, pain, or other issues due to different wounds being opened during a prosthetic component installation. In the example, tracking device 14 couples to two holes drilled femur 22. Similarly, tracking device 18 is coupled to two holes drilled in tibia 20. Thus, tracking device 14 and tracking device 18 are fixed to the bones of the musculoskeletal system. In one embodiment, surgical system 10 is registered to a mechanical axis of the leg such that movement of tibia 20 and femur 22 supports alignment of the leg to the mechanical axis. Surgical system 10 can be used to align bone cuts on tibia 20 and femur 22 to install the tibial prosthetic component and the femoral prosthetic component to produce an aligned leg.

Surgical navigation system 30 allows precise tracking of the position tracking device 14, tracking device 16, and tracking device 18 thereby tracking tibia 20 and femur 22. Tracking device 16 which supports a bone cut can be precisely placed relative to tibia 20 or femur 22. Tracking device 14 and tracking device 18 respectively relate to tibia 20 and femur 22 through a process of registration. The process of registration links a tracking device to the bone to which it couples. In the example, registration allows the tracking devices to precisely track a position of a first bone relative to a second bone. As an example or a registration process, navigation system 30 links the patient and the area of interest (the knee joint and leg) with a pre-operative scan. In one embodiment, the scan can be a CT scan, MRI scan, or a fluoroscope image. The process can include merging the physical space to the image space. For example, they can be paired point to point from a physical location to the location on the image. The computer 12 can then computer a 3D coordinate transformation of the physical and the image. The registration process is completed when the error is less than a predetermined amount. In one embodiment, the accuracy of surgical navigation system 30 is typically within 1-2 millimeters after the registration process has been completed successfully. In one embodiment, the registration process further includes identifying the locations of holes 32 and holes 34 relative to tibia 20 and femur 22. The location of holes 32 and holes 34 can be used to support registration of implanted devices 24 and 26 post-operatively. In one embodiment, the registration process of surgical navigation system 30 and the geometry of tracking devices 14 and 18 can be used to identify the location of holes 32 and 34 respectively on the femur 22 and tibia 20.

Surgical system 10 further includes implantable device 24 and implantable device 26. Implantable devices 24 and 26 are configured to be installed after the installation of the one or more prosthetic components and the surgical navigation system is removed. Implantable devices 24 and 26 have at least one anchor extending from enclosure 38 of implantable device 24 and enclosure 40 of implantable device 26. In the example, implantable device 24 has two anchors 36. Similarly, implantable device 26 has two anchors 36. The spacing of anchors 36 of implantable device 26 are configured to fit within holes 32 in femur 22 for holding tracking device 14. The spacing of anchors 36 of implantable device 24 are configured to fit within holes 34 in tibia 20 for holding tracking device 18. In other words, implantable devices 24 and 26 are configured to fit within the holes drilled to position and retain tracking devices 14 and 18. This concept supports intra-operative operative and post-operative monitoring of movement and position of the musculoskeletal system. A single wound used for installing one or more prosthetic components is required for the installation and use of surgical navigation system 30, implantable device 24, and implantable device 26. The concept can use known locations of holes 32 or holes 34 as identified by the surgical navigation system 30 for registration of implantable devices 24 and 26. Anchoring of implantable devices 24 and 26 to holes 32 and holes 34 are configured to reduce stress risers that can cause micro fractures or weakening of the bone long-term. In one embodiment, implantable devices 24 and 26 each have an inertial measurement unit (IMU) for measuring movement, position, and orientation. The position measurement system can also be a GPS chip, an acoustical ranging device, optical devices, inertial devices, magnetometers, inclinometers, or MEMs devices. Implantable devices 24 and 26 are configured to transmit measurement data to a computer or smart device. The location of the holes on tibia 20 and femur 22 can be provided for use in the registration of implantable devices 24 and 26. Alternatively, a registration process can be performed with the leg performing one or more predetermined movements with implantable devices 24 and 26 enabled to respectively link implantable devices 24 and 26 to tibia 20 and femur 22. Thus, surgical system 10 provides both intra-operative and post-operative movement, position, and orientation tracking. The measurement data from the IMU of implantable device 24 or device 26 can be used to determine range of motion, joint alignment, and gait mechanics after the prosthetic knee joint is installed. The measurement data can further be used to determine a regimen that optimizes user performance of the prosthetic knee joint to reduce rehabilitation time or allow increased activity or mobility.

A problem associated with drilling holes in bone of the musculoskeletal system is that the openings become stress risers. Stress concentrations can build up around the drilled holes. The stress can create weakness or fractures in the bone. Anchors 36 of implantable devices 24 and 26 are configured to fill the drilled holes from surgical navigation system 30 and reduce stress concentrations that can introduce problems. An adhesive can be used to retain anchors 36 within the holes 32 and 34. Alternatively, anchors 36 can have openings that support bone growth. A bone growth hormone can be introduced in holes 32 and 34 to grow in and around anchors 36 to strengthen the areas around holes 32 and 34. Finally, the threads on anchors 36 of implantable devices 24 and 26 can be designed to retain the anchors within the hole but reduce stress caused by the holes. In general, implantable devices 24 and 26 provides utility in monitoring motion and movement of the leg in support of rehabilitation, performance optimization, and reliability of the leg while reducing issue due to holes drilled for surgical navigation system 30.

In one embodiment, an external power source 30 can be provided to power implantable devices 24 and 26. The external power source 30 can be a device or system in proximity to the leg, can be incorporated in a wrap that is worn on around the knee joint after surgery, or can be a patch device that couples to the skin. External power source 30 can couple to implantable devices 24 and 26 via a radio frequency signal, inductive coupling, or pulsed or continuous energy waves that can penetrate the skin. Implantable devices 24 and 26 have power conversion circuitry to receive one or more signals and convert the one or more signals to energy that powers electronic circuitry. In one embodiment, the one or more signals can include communication with implantable devices 24 and 26. The communication can be received prior to the energy being from the one or more signals being converted to power electronic circuitry in implantable device 24 or implantable device 26.

Figure 2:
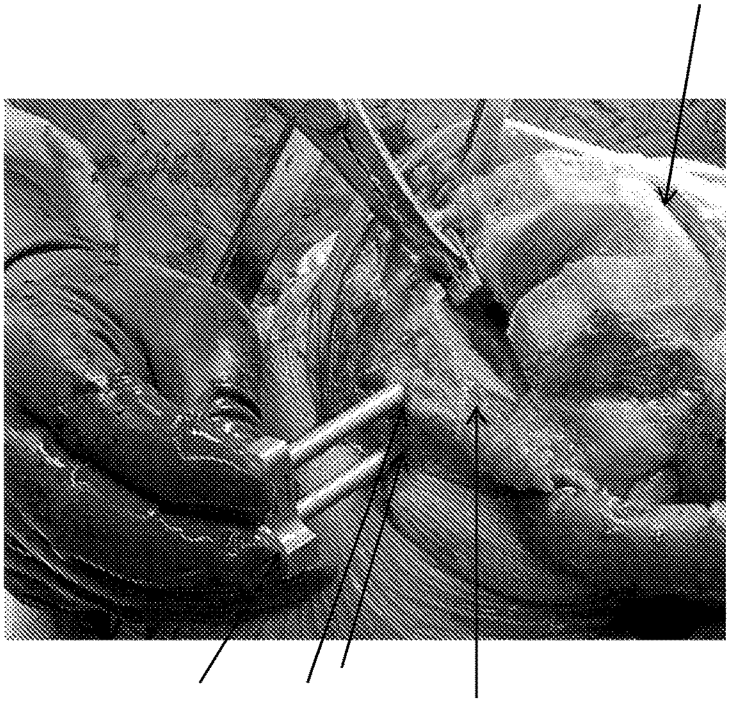
FIG. 2 is an illustration of an incision to expose a joint of the musculoskeletal system in accordance with an example embodiment.

FIG. 2 is an illustration of an incision to expose a joint of the musculoskeletal system in accordance with an example embodiment. Implanting a prosthetic component requires a wound be open to expose a region of the musculoskeletal system to provide access for resecting portions of the musculoskeletal system to fit the prosthetic component. In the example, a surgeon exposes a knee joint of the musculoskeletal system for installation of a prosthetic knee joint. Note that resections have been performed on both femur 22 and tibia 20. The wound exposes an area of the tibia below the resection that has sufficient bone to support mounting tracking device 18 to tibia 20. One or more holes are drilled in tibia 20 in the exposed region of the knee joint. In the example two holes 34 are drilled into tibia 20. A base of tracking device 18 is coupled to tibia 20. A base of tracking device 18 is positioned to couple to the tibia but does not impair the surgeon from modifying, installing, or testing the prosthetic knee joint. The remaining portion of tracking device 18 can be coupled to the base later during the prosthetic component installation. In general, holes 34 can be for other devices or equipment used during orthopedic surgery and is not limited to tracking device 14.

Figure 3:
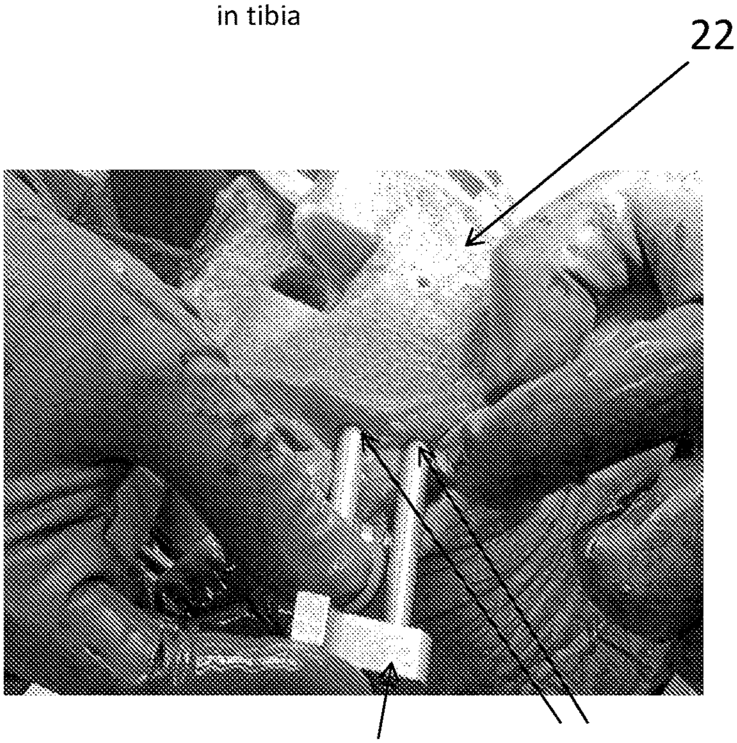
FIG. 3 is an illustration of the exposed region of the joint of the musculoskeletal system in accordance with an example embodiment.

FIG. 3 is an illustration of the exposed region of the joint of the musculoskeletal system in accordance with an example embodiment. In the example, femur 22 has been resected removing a portion of the bone material at a distal end. Note that the wound exposes the sides of the distal end of the femur below the resection. The side of the distal end of the femur has sufficient bone to support mounting tracking device 14 to femur 22. This location does not impair the surgeon from modifying, installing, or testing the prosthetic knee joint. One or more holes are drilled in femur 22 in the exposed region of the knee joint. In the example two holes 32 are drilled into femur 22. A base of tracking device 14 is coupled to femur 22. The remaining portion of tracking device 14 can be coupled to the base later during the prosthetic component installation. In general, holes 32 can be for other devices or equipment used during orthopedic surgery and is not limited to tracking device 14.

Figure 4:
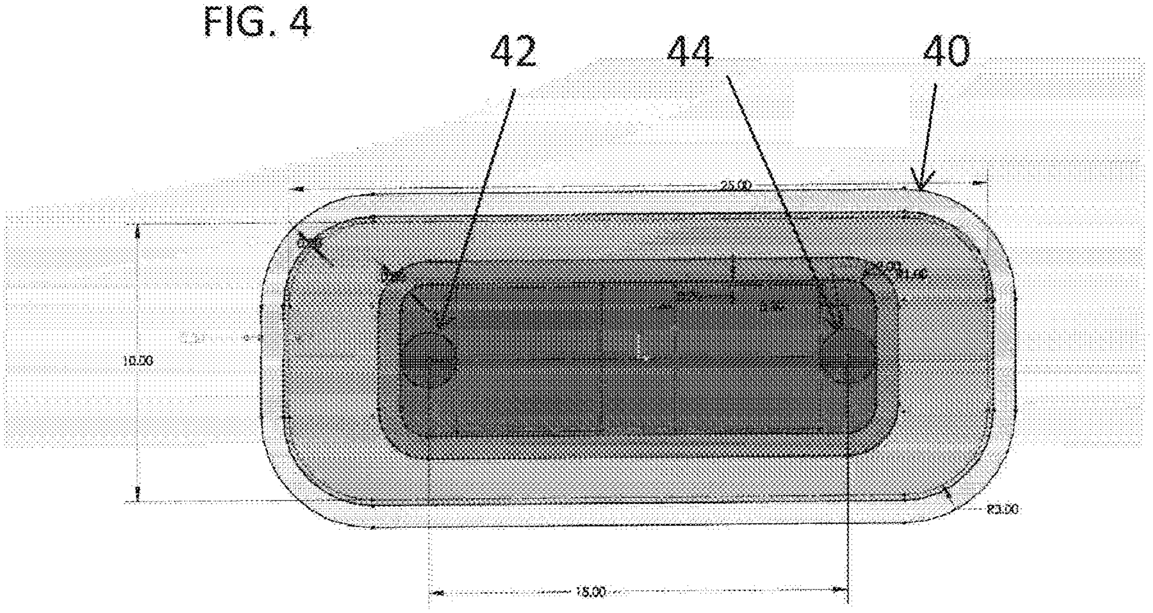
FIG. 4 is a top view of an enclosure for the implantable device in accordance with an example embodiment.

FIG. 4 is a top view of an enclosure 40 for implantable device 24 or implantable device 26 in accordance with an example embodiment. Enclosure 40 is hermetically sealed from an external environment. Enclosure 40 is made of bio-compatible materials for long-term implantation in the body. Enclosure 40 can comprise a plastic material such as polycarbonate, peek, polyurethane, or ultrahighmolecular weight polyurethane. Enclosure 40 can be made of flexible and comprise a silicone material or be rigid and comprise a metal or metal alloy. In the example, a length of enclosure 40 is approximately 25.0 millimeters and the width of enclosure 40 is approximately 10.0 millimeters. In general, enclosure 40 comprises an upper housing and a lower housing. In one embodiment, at least one anchor extends from enclosure 40 to couple to bone. In the example, an anchor 42 and an anchor 44 couple to and extend from the lower housing of enclosure 44. As shown, anchor 42 and anchor 44 are spaced 15 millimeters apart. Thus, holes 32 and 34 of FIGS. 2 and 3 are drilled with 15 millimeter apart center to center.

Figure 5:
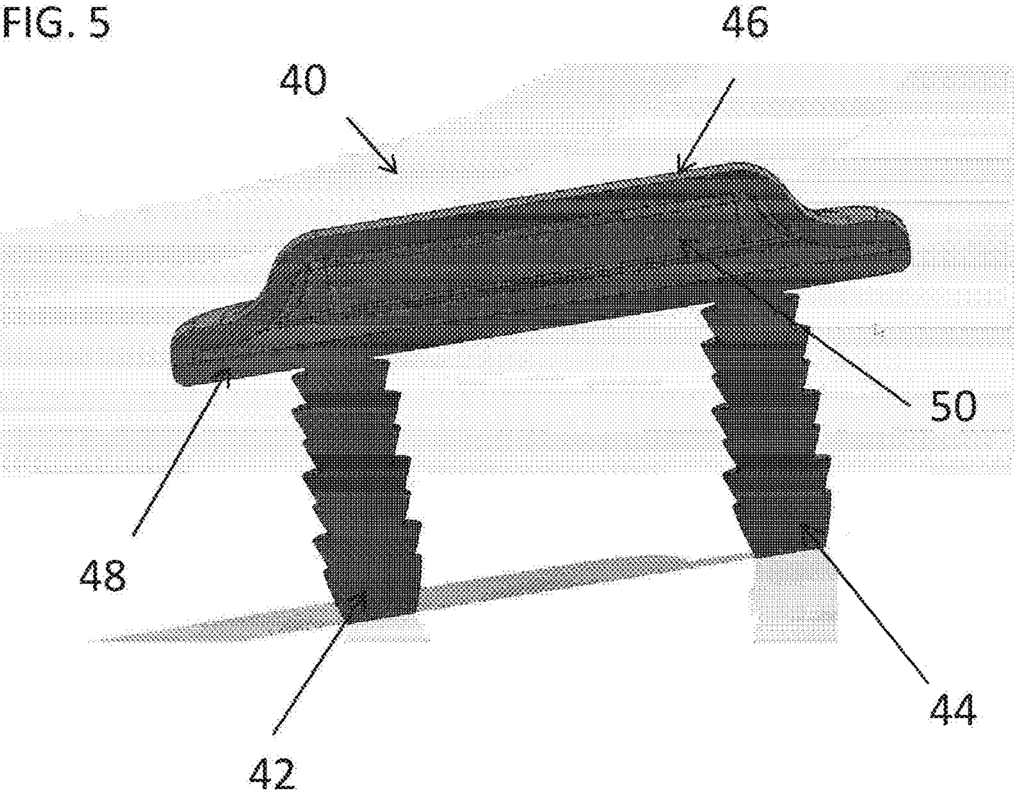
FIG. 5 is a cross sectional view of the enclosure for the implantable device in accordance with an example embodiment.

FIG. 5 is a cross sectional view of enclosure 40 for implantable device 24 or implantable device 26 in accordance with an example embodiment. In the example, enclosure 40 comprises upper housing 46 and lower housing 48. Upper housing 46 is sealed to lower housing 48 to form enclosure 40. In one embodiment, upper housing can be coupled together by adhesive or welded together for hermetic sealing. Enclosure 40 includes one or more cavities to house electronic circuitry, one or more IMUs, or one or more sensors. In the example, enclosure 40 has a single cavity to house electronic circuitry, an IMU, and one or more sensors. Anchors 42 and 44 extend from lower housing 48. Anchors 42 and 44 can comprise a different material than lower housing 48. In one embodiment, anchors 42 and 44 have threads configured to couple to bone. In one embodiment, anchors 42 and 44 are configured to push into holes 32 or holes 34 but are angled to prevent enclosure 40 from working free from the bone to which it couples. In one embodiment, the threads of anchors 42 and 44 are configured to reduce stress risers due to holes 32 or holes 34. Anchors 42 and 44 are configured to securely fasten enclosure 40 to bone.

Figure 6:
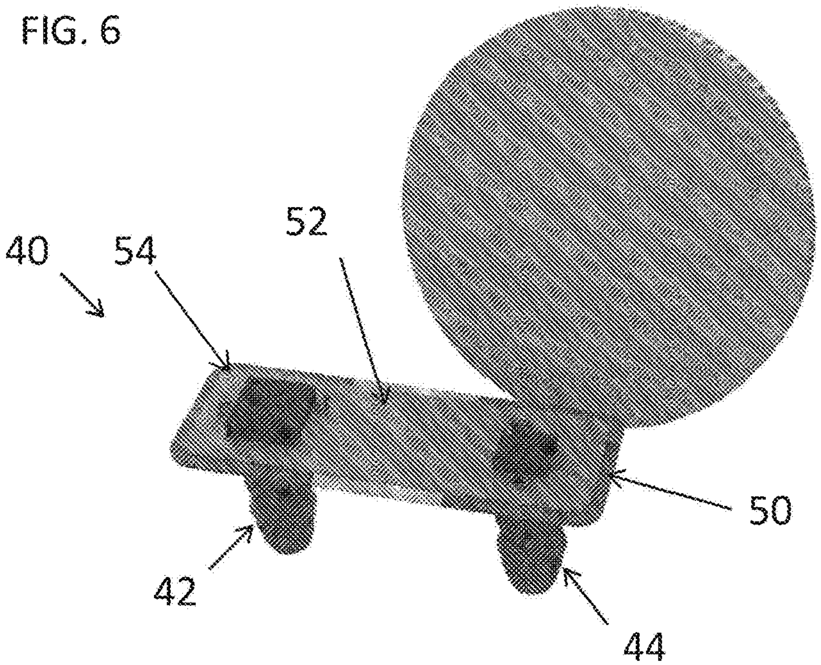
FIG. 6 is an illustration of a lower housing of the enclosure exposing a printed circuit board in accordance with an example embodiment.

FIG. 6 is an illustration of the lower housing 50 exposing a printed circuit board 52 in accordance with an example embodiment. Upper housing 46 of FIG. 5 is removed from enclosure 40. Enclosure 40 can include one or more printed circuit boards. In the example, a single printed circuit board 52 is coupled to lower housing 46. In one embodiment, electronic components are coupled to printed circuit board 52. Printed circuit board 52 includes one or more layers of interconnect to couple the electronic components together to form electronic circuitry 54. Electronic circuitry 54 couples to at least one IMU to provide movement, position, and orientation measurement data. In one embodiment, electronic circuitry 54 does not have a local power supply. As mentioned previously, electronic circuitry 54 is configured to receive energy from external power source 28 of FIG. 1 until sufficient power is received to support the generation of measurement data for a predetermined period of time. In one embodiment, external power source 28 can continuously provide energy to keep electronic circuitry 54 enabled indefinitely. Electronic circuitry 54 is configured to control a measurement process and transmit measurement data to a computer. In one embodiment, the computer can be a PC, tablet, smartphone, or a medical device. The computer can process the measurement data and translate the measurement data to useful information that is used by the surgeon, a doctor, medical staff, or the patient. Electronic circuitry 54 can further couple to one or more sensors. The one or more sensors can be configured to support pain mitigation, infection detection, rehabilitation, or joint performance.

Figure 7:
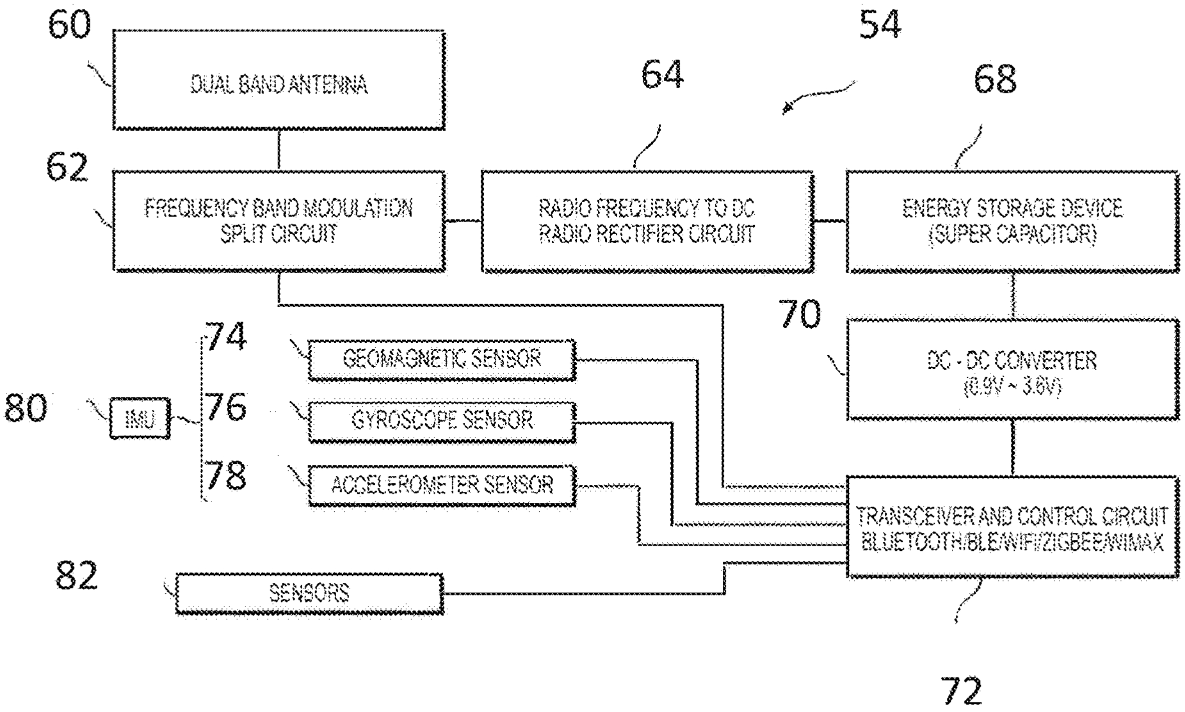
FIG. 7 is a block diagram of electronic circuitry in accordance with an example embodiment.

FIG. 7 is a block diagram of electronic circuitry 54 in accordance with an example embodiment. In one embodiment, electronic circuitry 54 is not self-powered but is configured to receive energy from a remote source, store the energy, and use the energy to perform at least one task after the stored energy is above a predetermined threshold. In general, electronic circuitry 54 is enabled when sufficient energy is stored to perform a measurement sequence and transmit measurement data to a device, computer, internet, or processor configured to receive the measurement data. The energy can be electromagnetic, light, radio frequency, pulsed energy, or other form capable of being coupled through skin. In the example, external power source 28 of FIG. 1 can be a device that is placed in proximity to implantable devices 24 or 26 of FIG. 1. For example, external power source 28 of FIG. 1 can transmit a radio frequency signal configured to skin to implantable device 24 or implantable device 26 of FIG. 1. External power source 28 of FIG. 1 can include a battery that powers a transceiver for transmitting a radio frequency signal. In general, a frequency less than 1 gigahertz is desirable for good skin penetration. Alternatively, external power source 28 of FIG. 1 can include an inductor that electromagnetically couples to an inductor in implantable device 24 or implantable device 26 for delivering energy.

Implantable devices 24 or 26 can be powered by external power source 28 by receiving and converting an energy wave. In one embodiment, the signal or energy wave is harvested by circuitry within electronic circuitry 54 to power electronic circuitry 54 after sufficient energy is stored. As mentioned previously, electronic circuitry 54 couples to an IMU to support movement, position, and orientation measurement. In one embodiment, electronic circuitry 54 can further couple to one or more sensors 82 or circuitry for providing measurement data or to electronic circuitry that provides therapy. Electronic circuitry 54 includes a transceiver to transmit measurement data and receive information in real-time. Electronic circuitry 54 is configured to couple to a computer configured to process the measurement data. Electronic circuitry 54 is configured to control a measurement process and transmit the measurement data. Electronic circuitry 54 is used in implantable devices 24 and 26 of FIG. 1. In general, implantable devices 24 or 26 are directly coupled to bone so movement or placement of the implantable devices 24 or 26 relative to the bone is fixed and cannot change over time. Moreover, implantable devices 24 or 26 reduce stress risers due to holes drilled in bone for surgical navigation system 30 of FIG. 1 and are coupled to bone without causing a wound as it is placed during prosthetic component installation.

Electronic circuitry 54 comprises a dual band antenna 60, a frequency band modulation split circuit 62, a radio frequency to DC radio rectifier circuit 64, an energy storage device 68, a DC-DC converter 70, a transceiver 72, and an IMU 80. Electronic circuitry 54 can include control logic a processor, digital signal processing, microcontroller, digital logic, memory, or software programming to support a process or function for implantable devices 24 or 26. In one embodiment, transceiver and control circuit 72 can comprise one or more of Bluetooth, Bluetooth Low Energy (BLE), Zigbee, Wimax, Wifi, or other communication circuitry. Electronic circuitry 54 can further include sensors 80 to monitor and generate measurement data. Sensors 80 can include one or more devices configured to provide a therapy or improve health to the musculoskeletal system, bone, or surrounding areas. Electronic circuitry 54 includes at least one antenna configured to receive or transmit a signal or energy wave. In one embodiment, electronic circuitry 54 includes a dual band antenna 60 can comprising two separate antennas each optimized for a specific frequency. In general, electronic circuitry 54 operates at two or more frequencies. In the example, a first antenna of dual band antenna 60 operates at a frequency below 1 gigahertz to support efficient transfer of energy via radio frequency signal below the skin. The 1 gigahertz frequency or below can be selected in the industrial, scientific, or medical (ISM) frequency band. The second antenna of dual band antenna 60 can be tuned to a frequency depending on the application. Although the lower frequency (1 gigahertz) will be more efficient in energy transfer both frequencies can be used to harvest energy. In one embodiment, the second antenna operates at a frequency associated with an I.E.E.E. standard that has wide acceptance and supports wireless communication such as Zigbee, WiFi, Bluetooth, Bluetooth Low Energy (BLE), or WiMax but is not limited to such. These standards support communication and the transmission of data. Some of these standards support low power and medium to short range transmission. In one embodiment, a batteryless device such as implantable devices 24 or 26 of FIG. 1 having electronic circuitry 54 will use a Bluetooth Low Energy (BLE) transceiver to minimize power use. A BLE transceiver is configured to communicate with any Bluetooth device. The BLE transceiver operates at reduced power that reduces the requirements of energy storage device 68 thereby reducing energy storage requirements to operate electronic circuitry 54 and supports a smaller form factor. Typically Bluetooth operates at 2.4 gigahertz and supports high speed data transfer within a 10M radius.

Dual band antenna 60 receives a radio frequency signal. Frequency band modulation split circuit 62 couples to dual band antenna 60 and removes information that is carried on the radio frequency signal. In one embodiment, the received radio frequency signal is in the ISM band at 915 megahertz. The information is provided to transceiver and control circuit 72. Transceiver and control circuit 72 is configured to use information from the radio frequency signal, control a measurement process, and transmit measurement data. The radio frequency signal (with information removed) is provided by frequency band modulation split circuit 62 to radio frequency to DC radio rectifier circuit 64. In general, the radio frequency signal is a low power signal. In one embodiment of radio frequency to DC radio rectifier circuit 64, an input matching circuit couples to dual band antenna 60 to efficiently convert an electromagnetic signal to an electrical signal. The electrical signal is then coupled to a rectifier circuit that produces a DC voltage.

Radio frequency to DC radio rectifier circuit 64 couples to energy storage device 68. As it name implies, energy storage device 68 stores energy that will be used to enable electronic circuitry 54. There are many types of energy storage devices that can be used such as an inductor, a battery, a capacitor, magnetic storage, electrochemical storage, or chemical storage to name but a few. In the example, energy from radio frequency to DC radio rectifier circuit 64 is stored on a super capacitor. Energy storage device 68 is configured to store sufficient energy to operate electronic circuitry 54 for a predetermined time period after the radio frequency signal is no longer received. In one embodiment, energy storage device 68 charges for approximately 10 seconds before electronic circuitry 54 is enabled. In one embodiment, the charge in energy storage device 68 is sufficient to generate measurement data and transmit the measurement data to another device.

Energy storage device 68 couples to DC-DC converter 70. DC-DC converter 70 is configured to generate one or more voltages to power electronic circuitry 54. Typically, the voltage on energy storage device 68 is lower than needed. DC-DC converter 70 multiplies the voltage to a usable value for electronic circuitry 54. In one embodiment, DC-DC converter generates one or more voltages from 0.9 volts to 3.6 volts. DC-DC converter 70 couples to transceiver and control circuit 72 to power a measurement process. Control circuit 72 can comprise a microprocessor, digital logic, application specific circuitry, microcontroller, digital signal processor, analog circuitry or other circuitry to control the measurement process. In one embodiment, transceiver and control circuit 72 is not enabled until energy storage device 68 stores a predetermined amount of energy. Once enabled, transceiver and control circuit 72 controls a measurement process and is configured to transmit measurement data. Transceiver and control circuit 72 can include memory. The memory can be used to store software, calibration data, measurement data, programs, workflows, or other information. IMU 80 and sensors 82 couple to transceiver and control circuit 72. In one embodiment, implantable devices 24 or 26 having electronic circuitry 54 will include IMU 80 for movement, position, and orientation measurement thereby monitoring movement, position, or orientation or relational movement, position, or orientation between two or more devices similar to intra-operative surgical navigation system 30 of FIG. 1. In one embodiment, IMU 80 comprises a geomagnetic sensor 74, a gyroscope sensor 76, and an accelerometer sensor 78. IMU 80 is configured to measure 6 degrees of freedom comprising translation movement along the X, Y, and Z axis as well as rotational movement such as yaw, roll, and pitch around each axis. Sensors 82 can differ in implantable device 24 or implantable device 26 as is configured to measure one or more parameters of interest and may differ depending on the specific application for each implantable device. In one embodiment, electronic circuitry 54 can include energy harvesting circuitry to couple energy to energy storage device 68. The energy harvesting circuitry can use motion of the musculoskeletal system to generate energy.

Figure 8:
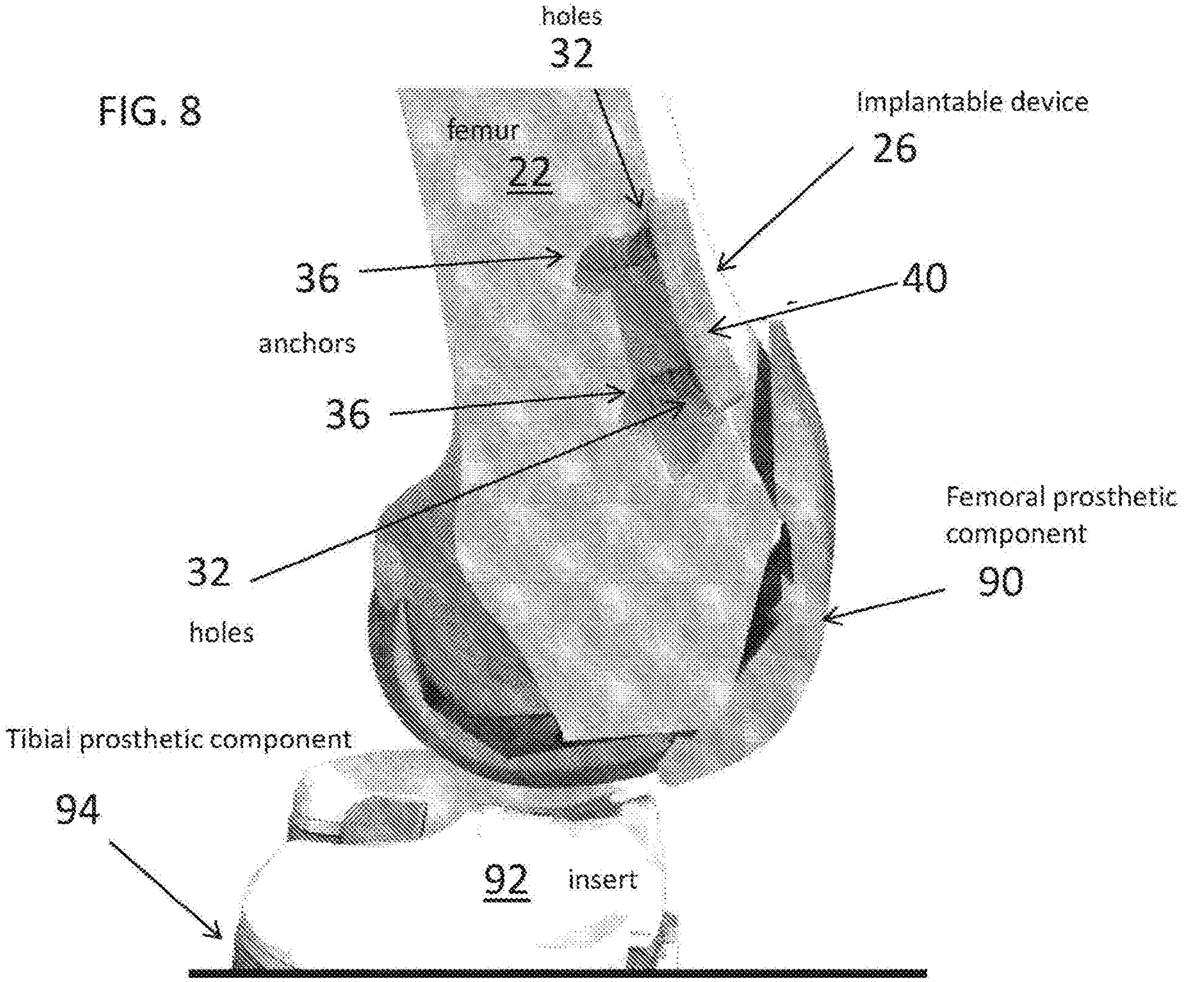
FIG. 8 is a cross-sectional view of the implantable device inserted in the holes of the femur in accordance with an example embodiment.

FIG. 8 is a cross-sectional view of implantable device 26 inserted in holes 32 of femur 22 in accordance with an example embodiment. In one embodiment, implantable device 26 is coupled to holes 32 drilled in femur 22 to support and retain tracking device 14 of surgical navigation system 30 of FIG. 1. Holes 32 in femur 22 comprise two holes. Surgical navigation system 30 of FIG. 1 is configured to support installation a knee joint comprising femoral prosthetic component 90, insert 92, and tibial prosthetic component 94. Navigation system 30 of FIG. 1 is removed after the installation of the knee joint. Implantable device 26 and implantable device 24 (not shown) are respectively placed in holes 32 and holes 34 (not shown). Anchors 36 of implantable device 26 are pressed into holes 32 in femur 22. Threads of anchors 36 couple to bone adjacent to holes 32 in femur 22. In one embodiment, anchors 36 retain implantable device 26 to femur 22 and resist implantable device from pulling out of holes 32. In one embodiment, the threads of anchors 36 engage to the areas of the bone adjacent to holes 32 as shown in FIG. 8. The threads are configured to reduce or eliminate stress risers that can structurally weaken the bone near holes 32 and pose a long-term risk. In the example, enclosure 40 of implantable device 26 is flexible and is configured to conform to contours of the bone when anchors 36 couple to femur 22. In one embodiment, implantable device 26 is a permanent implant coupled to a fixed position to femur 22. Implantable device 26 is an in-wound sub-dermal permanent device that did not require additional surgery or incisions for installation. Implantable device 26 can prevent stress risers from holes drilled to mount tracking device 14 of surgical navigation system 30. Anchors 36 can reduce stress adjacent to holes 32. Holes 32 can be filled with an adhesive with anchors 36 to reduce fracturing. Anchors 36 can be made porous with holes 32 filled with bone growth hormone to support bone growth through anchors 36 to bone adjacent to holes 32 to reduce fracturing or stress risers. Implantable device 26 including IMU 80 can monitor position, movement, and orientation of femur 22. Moreover, locations of holes 32 can be registered by surgical navigation system 30 of FIG. 1 and provided to the computer or implantable device 26 to simplify a registration process or reduce error in measuring movement, position, or orientation. Implantable device 26 can provide reliable measurement data because implantable devices have a known location that will not shift over time.

Figure 9:
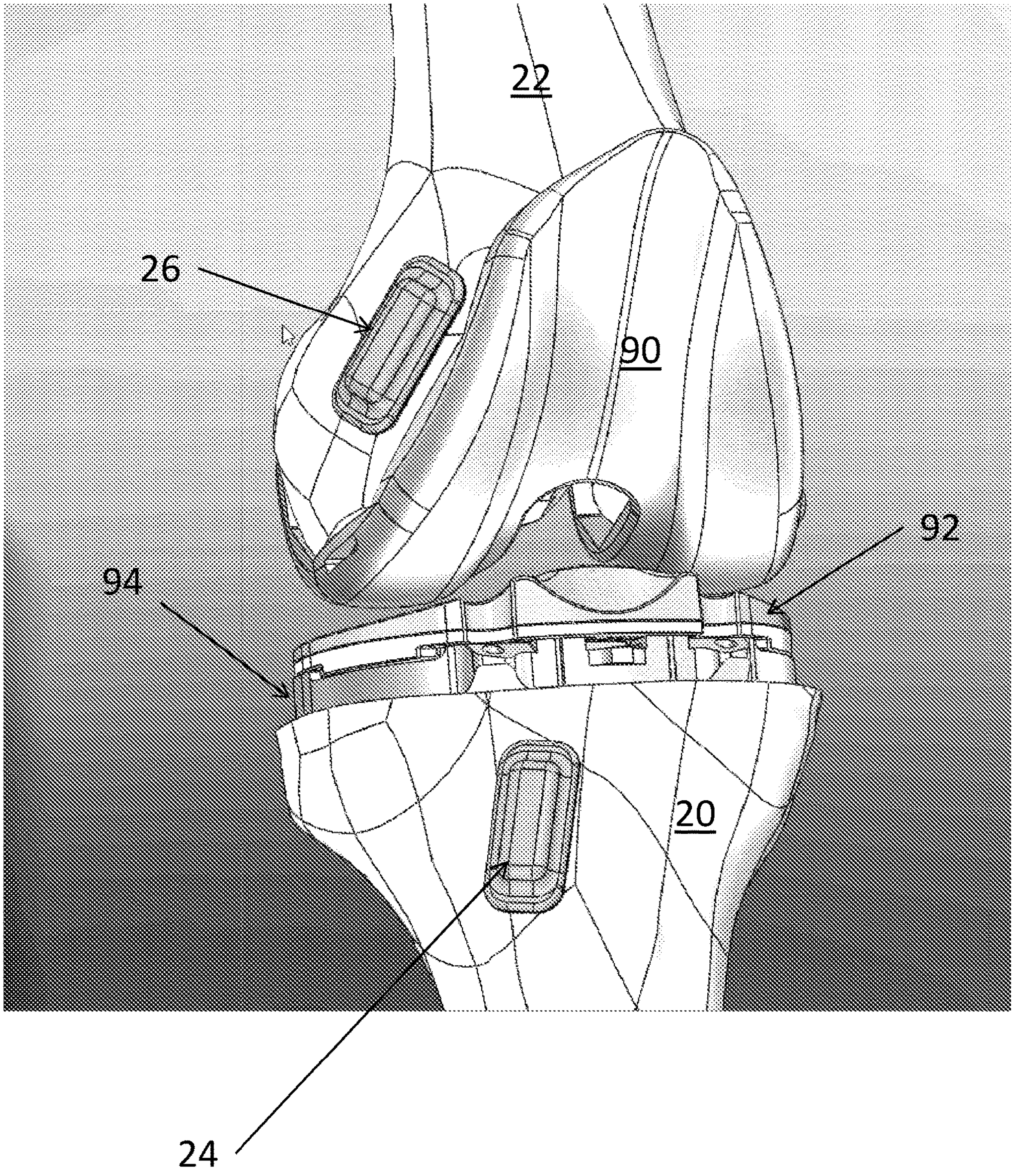
FIG. 9 is an illustration of the joint of the musculoskeletal system in accordance with an example embodiment.

FIG. 9 is an illustration of a joint of the musculoskeletal system in accordance with an example embodiment. One or more prosthetic components are installed during surgery to replace a joint of the musculoskeletal system. An incision or wound is made to provide access to the joint to prepare bone for receiving the one or more prosthetic components. The surgical system 10 of FIG. 1 comprises a surgical navigation system 30, implantable device 24, and implantable device 26. Holes 32 and 34 are drilled as shown in FIGS. 3 and 4 to couple tracking devices 14 and 18 of surgical navigation system 30 to femur 22 and tibia 20. Surgical system 10 of FIG. 1 supports installation of femoral prosthetic component 90 to femur 22, tibial prosthetic component 94 to tibia 24, and insert 92. In one embodiment, insert 92 couples between tibial prosthetic component 94 and femoral prosthetic component 90. Insert 92 has a low friction surface and is configured to support movement of the leg. Surgical navigation system 30 of surgical system 10 of FIG. 1 measures movement, position, or orientation of femur 22 and tibia 20 to align and balance the knee joint intra-operatively. Implantable devices 24 and 26 are respectively coupled to tibia 20 and femur 22 upon removing tracking devices 14 and 18 after the knee joint is installed. As previously mentioned implantable devices 24 and 26 each have an IMU 80 with electronic circuitry 54 as shown in FIG. 7. Implantable devices 24 and 26 support measurement of position, movement, or orientation post-operatively using holes 32 and 34 of FIGS. 2 and 3. In the example, implantable devices 24 and 26 can measure movement of femur 22 relative to tibia 24, rotation of the knee joint, anterior-posterior movement, an range of motion to name but a few. Note that holes 32 and 34 are located in areas exposed by the wound for installing femoral prosthetic component 90, tibial prosthetic component 94, and insert 92. Thus, surgical system 10 supports position, movement, or orientation measurement of the musculoskeletal system intra-operatively and post-operatively.

Implantable devices 24 and 26 can have one or more sensors or circuitry to provide therapy. The measurement data from the one or more sensors and the IMU can be transmitted to a computer or device where the information can be processed and delivered to a user such as a surgeon, doctor, healthcare worker, or patient. In one embodiment, the measurement data can further be used to determine a regimen that optimizes user performance of the prosthetic knee joint to reduce rehabilitation time or allow increased activity or mobility. In one embodiment, implantable devices 24 and 26 can include cameras, optical sensors, or light emitting diodes to monitor regions in proximity to the knee joint. Monitoring synovial fluid near a joint of the musculoskeletal system can be used to determine infection via color or turbidity. Sensors to monitor pH or temperature can also be used to indicate infection activity in or near the joint. Sensors to detect micromotion of the prosthetic components coupled to femur 22 or tibia 20 can indicate stability of the adhesive holding the prosthetic component to bone. Implantable devices 24 and 26 can also be used to provide therapy for improving the musculoskeletal system, healing a fracture, or measuring bone density. Implantable device 24 and 26 can have circuitry to mitigate pain due to the joint circuitry thereby decreasing rehabilitation time. Thus, the use of implantable devices 24 and 26 can provide substantial benefits by generating quantitative measurement data related to the musculoskeletal system. The computer receiving measurement data from implantable devices 24 and 26 can include one or more computer programs to analyze the measurement data, utilize the measurement data in a process, procedure, workflow, or review, and further transmit the measurement data or results to a patient, doctor, surgeon, or other medical staff to support patient health.

In general, implantable devices 24 and 26 coupled to the musculoskeletal system can be used on a knee joint, shoulder joint, hip, spine, ankle, wrist, fingers, toes, or elbow joint to monitor movement, position, or orientation. The physical parameter or parameters of interest that can be coupled to electronic circuitry 54 of FIG. 7 are temperature, blood oxygenation, pressure, sound, pH, SaO2, humidity, barometric pressure, height, length, width, tilt/slope, position, orientation, load magnitude, force, pressure, displacement, density, viscosity, light, color, sound, optical, vascular flow, visual recognition, alignment, rotation, inertial sensing, turbidity, strain, angular deformity, vibration, torque, elasticity, motion, acceleration, infection detection, pain inhibition, magnetic, gyroscopic, infrared, chemical sensing, biological sensing, and energy harvesting to name but a few. Often, two or more measured parameters are used in conjunction with another to perform a clinical assessment. Data collection of measurement data can be stored in the computer or provided to a database for further analysis. A graphical user interface can support assimilation of measurement data. The measurement data can be periodically measured and transmitted to a computer for further processing.

The computer configured to receive measurement can include software that analyzes the measurement data from implantable devices 24 and 26 to measure gait mechanics that include stride, cadence, activity, and steps. The computer can further include a program that uses the measurement data for a kinetic assessment that includes balance, stability, rotation, graft adherence, graft failure proprioception, range of motion, or muscle strength. Wearing a sensored knee brace prior to an operation can provide patient data that provides information related to pain, activity level, range of motion, and other factors that provides knowledge on the issues the patient is having and how to address a prosthetic component installation that supports a satisfactory patient outcome. In one embodiment, the computer can be a cell phone, tablet, or small device that includes an app. Implantable devices 24 and 26 provide measurement data to the app in the cell phone, tablet, or small device that monitors movement, exercise, or other sensor information. The information related to rehabilitation can be provided to a doctor or staff for review. Data analytics using the measurement data from implantable devices 24 and 26 can be used to modify a therapy to improve results or indicate that the knee joint is fully healed and normal activity can be resumed. Recorded movement or motion can be displayed on a display or compared with prior measurement data to indicate progress. Milestones or issues can be detected using the measurement data and sent to the patient or to a doctor and staff. The doctor or staff can contact the patient if an issue requires a change in a workflow. Measurement data from implantable devices 24 and 26 can be used to determine when an office visit occurs.

In one embodiment, implantable devices 24 and 26 can be in two-way communication electronic circuitry with each other. In one embodiment, communication can occur over a single frequency band. Alternatively, two-way communication can occur over two or more different frequencies. In one embodiment, a handshake can occur between implantable device 24, implantable device 26, and the external computer before communications are established.

Examples of uses for implantable devices 24 and 26 are disclosed herein below after the one or more prosthetic components have been installed. In the example, devices 24 and 26 are in fixed positions coupled to tibia 20 and femur 22 and are in-wound or sub-dermal implanted devices. Devices 24 and 26 correspond to navigation system 30 in function. The examples will be for the knee but can be adapted for any joint or region of the musculoskeletal system. A system comprises implantable device 24, implantable device 26, and a computer configured to receive and process measurement data. In one embodiment, there may be one or more external power sources to provide power to implantable devices 24 and 26. In one embodiment, a transceiver in proximity to implantable devices 24 and 26 to receive measurement data from implantable devices 24 and 26. The transceiver can then transmit the measurement data to the computer. In one embodiment, the transceiver can be an energy source to power implantable devices 24 and 26. In one embodiment, the leg is taken through a full ROM, full extension, and defined flexion is recorded by the computer configured to receive measurement data from implantable devices 24 and 26. Measurement data related to rotation, dynamic stresses, and translation can also be recorded by the computer. In one embodiment, an anterior-posterior drawer is performed where the knee is flexed 90 degrees and a force applied to the tibia in the posterior and then in the anterior direction. The translation and displacement of the knee is recorded relative to implantable devices 24 and 26. A Lachman Test can also be performed where the knee is flexed 20 degrees and the tibia is pulled forward to assess the amount of anterior motion of the tibia to define ACL stability. Similarly, medial-lateral forces can be applied at 20 degrees to define collateral ligament stability.

Implantable devices 24 and 26 are also used for post-operative monitoring. First, implantable devices 24 and 26 can be used to identify if the patient post-operative therapy is progressing appropriately. In one embodiment, the patient is discharged with crutches and a brace. Implantable devices 24 and 26 can be in communication with a smartphone of the patient, surgeon, doctor, or healthcare provider. Physical Therapy is instituted within several days of surgery. Limited weight bearing is controlled to protect the ACL until interval healing has occurred and the patient's quadriceps function and knee stability has returned. The knee is monitored for infection and resolution of swelling and inflammation. Compliance to the prescribed post-operative regimen can be monitored. An exercise regimen can be sent to the patient's phone and implantable devices 24 and 26 are activated to monitor that the patient is following protocol and remains in a "safe" healing zone. A knee brace can house the external energy source to energize implantable devices 24 and 26, and the knee function can then be interrogated.

Placement of implantable devices 24 and 26 in the femur 22 and tibia 20 are used to describe knee function. For example, implantable devices 24 and 26 can monitor and measure ROM (range of motion) relative to gravity and the femur 22 and tibia 20. Implantable devices 24 and 26 can be used to measure quadriceps strength and torque with a defined extension maneuver with applied resistance. Gait mechanics such as stride, cadence, activity, steps and other movement can be monitored by implantable devices 24 and 26. All of the above quantitative measurement data is used to support assessment of the patient post-operatively. The measurement data can indicate if adjustments to the therapy are required and the status of the implanted prosthetic components.

In the example of a knee joint, the quantitative measurement data from the implantable devices 24 and 26 can indicate stable knee function. The patient can then be released from using crutches and later bracing can be considered to support the knee joint for optimal operation. The effects of the therapy program using implantable devices 24 and 26 can be linked to knee function and a patient can be educated on their recovery relative to a plan and other patients. In one embodiment, when implantable devices 24 and 26 are activated, the data will be transmitted (RF/Bluetooth) to a patient recovery application. In one embodiment, the application can be on a computer or a device such as a smart phone. The quantitative measurement data from implantable devices 24 and 26 will be uploaded into a cloud based VPN (virtual private network) that is HIPPA Compliant. The quantitative measurement data can be assessed by one or more computer programs and updates, work flows, and the measurement data can be sent to the treating physician and health care team. Implantable devices 24 and 26 can be used to support post-op exercises, treatment, or pharmaceuticals that can accelerate the healing phase. Furthermore, different ACL reconstruction techniques can be compared with real-time data. Evaluations of the effects of ACL reconstruction when combined with multi ligamentous injuries can also be analyzed. Healing phase monitoring related to graft adherence to the host tunnels (bone to bone, tendon to bone, composite to bone) can provide quantitative measurement data related thereto. Other important parameters can also be generated such as improving ROM and terminal extension, achieving improved muscle strength, improved proprioception, improved stability, and improved gait mechanics.

Implantable devices 24 and 26 can also be used to determine when the "patient" is healed. For example, quantitative measurement data from implantable devices 24 and 26 can be used to determine if an ACL is healed so that the patient can return to high intensity activities. Presently, a patient exam is often used after a predetermined time after surgery to release a patient to sports. The patient exam is a subjective examination that can vary from significantly between surgeons and doctors. There is very little objective data that is utilized to define when functional healing has occurred. A quantitative functional knee exam can be performed with the activated implantable devices 24 and 26 relaying the information in real-time. Further evaluation, can be assessed while the patient is placed in a walking regimen, then a running regimen, followed to sports related acceleration—deceleration activities where data is being generated by implantable devices 24 and 26. In one embodiment, implantable devices 24 and 26 will send data related to the knee function to a data base for evaluation by one or more programs that use the quantitative measurement data to provide a functional knee determination based on measurement data of a healed functional knee that can be used with a subjective examination.

Implantable devices 24 and 26 can also be used to evaluate post-operative exercises, post-operative treatment, or pharmaceuticals where measurement data provides evidence of the efficacy of the different treatments. Different techniques to reconstruct the musculoskeletal system can also be evaluated. For example, different ACL reconstruction techniques can be compared with real-time data to evaluate the effects of ACL reconstruction when combined with multi ligamentous injuries. In one embodiment, the healing phase monitoring is related to the graft adherence to the host tunnels such as bone to bone, tendon to bone, or composite to bone. Other important parameters can also be monitored to see the efficacy of the treatments to improve range of motion, terminal extension, muscle strength, improved proprioception, improved stability, or improved gait mechanics.

Implantable devices 24 and 26 can also be used for long term monitoring. An extreme example is an athlete returning back to a sport. For example, a knee joint can be monitored for skeletal knee stability related to strength. The torque and range of motion can be monitored during specific training or activities that are deemed essential. The measurement data can be analyzed from implantable devices 24 and 26 that lead to specific interventions that can be utilized if knee stability is decompensating. Furthermore if the athlete fells that a sprain or injury occurred and wants to continue playing, the screw can be activated and the knee mechanics and kinetics of the leg and joint can be evaluated. Although the example is a knee joint it should be noted that the use of implantable devices 24 and 26 can be used for any joint or part of the musculoskeletal system.

As previously mentioned, there are many different types of sensors that can be utilized within implantable devices 24 and 26. In one embodiment, implantable devices 24 and 26 can be used for the treatment of disease or apply a treatment or drug. For example, implantable devices 24 and 26 can include an ultrasonic sensor that can be utilized to generate frequencies to aid in healing through blood flow modulation, and osteoplastic induction. Implantable devices 24 and 26 have the ability for in vivo monitoring of multiple parameters with multiple sensors. The stability of implantable devices 24 and 26 implantation can be monitored to measure local bone softening due to blood flow and final healing of graft. The stability of a joint related to motion, rotation, translation, and range of motion. From a macro perspective, implantable devices 24 and 26 can be used to monitor the musculoskeletal system to provide measurement data related to joint mechanics as muscle strength changes, gait mechanics, compliance to rehabilitation program (frequency, effort, protection), general activity, patient directed interrogation of the musculoskeletal system, and physician interrogation of the musculoskeletal system related to a joint, rehabilitation, and sports.

As shown herein above, implantable devices 24 and 26 can be placed in the femur 22 and tibia 2—to provide quantitative measurement data that can be used in a variety of ways to assess the musculoskeletal system and more specifically a knee joint replacement and subsequent rehabilitation of the leg. In general, implantable devices 24 and 26 will be used in the sports medicine to assess the musculoskeletal system, repair, and rehabilitate using quantitative measurement data. The measurement data on the knee, hip, and rotator cuff, shoulder, and other musculoskeletal repairs can be used to ensure that the subject is prepared and ready for sustained physical activity.

Implantable devices 24 and 26 can be used in trauma applications such as hip-pelvis, spine, and extremity fractures. Hip fractures can be stabilized with a screw attached to a rod or plate. Implantable devices 24 and 26 can aid in providing measurement data related to the internal stability of the bone when placing the screw. Post-operatively, implantable devices 24 and 26 can be used to monitor healing of the fracture. Implantable devices 24 and 26 will house micro-electronics, sensors, communication circuitry, and logic to control a measurement process. In one embodiment, implantable devices 24 and 26 will include micro-motion related sensors. Signals can be sent through the fracture side to be detected by micro-motion sensors to determine the effects of weight bearing on the fracture. Surgeons can refine the patient's post-operative activities and gait mechanics during the healing process. Moreover, the surgeon or doctor can assure the patient with quantitative measurement data related to their progress and send activity strengthening exercises related to gait or strength to meet the need of the patient.

Implantable devices 24 and 26 can be used to detect motion at an implant to bone interface or bone to bone interface. For example, implantable devices 24 and 26 can be used to detect motion in the spine between an implant and vertebra interface. In spinal surgery, implants such as interbody fusion cages and disc replacement prostheses are often used. In most fusion or corrective spinal procedures, pedicle screws are used. Spinal pain following fusions, disc replacements, and other procedures can stem from persistent motion at what should be a stable interface. In certain instances a surgeon wants the ability to detect motion at an implant or bone interface. An example of movement is when a spinal segment is fused; the forces are then transferred to the surrounding soft tissue and vertebral levels above and below. Proximal Junctional Kyphosis, is where the spinal segment above and/or below the fused segment becomes unstable can occur asymptomatically. Further surgery may be required when symptoms occur, to stabilize the segment. This can occur continuously throughout the patient's life. Currently, it is difficult to identify the cause of significant post-operative spinal pain. Abnormal motion is currently evaluated by standard and dynamic motion X-rays, and nuclear imaging. Presently there is no accurate way to confirm abnormal motion at these interfaces with a high sensitivity and specificity. Moreover, a surgeon desires the ability to avoid surgical exploration of the fusion or disc implant site to confirm abnormal motion.

Implantable devices 24 and 26 are an implantable sensor system that is applied at the bone-implant surface. Since a spinal fusion requires integration of the "cage" or spinal instrumentation into the fusion mass, a sensor that is incorporated into the "cage" or instrumented elements can detect motion. In non-instrumented fusions, the sensors can be implanted into the bony elements at specific locations to detect abnormal motion post-operatively. In one embodiment, a spinal implant such as implantable devices 24 and 26 are inserted into the pedicle of a spinal bone. The implantable devices 24 and 26 will house the micro-electronics. Implantable devices 24 and 26 are activated with one or more sensors that measures position in 3D space and trajectory such that implantable devices 24 and 26 can be guided into appropriate angles and depth within bone. Implantable devices 24 and 26 will be placed then tested for stability and torque to confirm implantable devices 24 and 26 are fully seated. Each spinal segment will house at least two implantable devices having a form factor that can be used with the spine and can be placed into the spinal segment above and below the surgical segments. Post-operatively, the sensors implantable devices 24 and 26 can be activated or powered by an external mechanism. For example power can be provided inductively or by radio frequency signals to provide power that enables implantable devices 24 and 26 for providing quantitative measurement data. A capacitor or energy storage device can store the energy for use at a later time period or when activated. Power management circuitry can be used to reduce energy consumption. Alternatively, implantable devices 24 and 26 could house an energy source such as a battery. Once implantable devices 24 and 26 are activated, the patient would flex, extend, rotate and load the sensors in implantable devices 24 and 26 at variable positions. In one embodiment, the sensor information would be transmitted from implantable devices 24 and 26 and received by an external computer with a display. The computer can include software to analyze the quantitative measurement data, display the measurement data, or the measurement data can be translated in a graphic form to support rapid assimilation of the information. The surgeon can now document the amount of motion and load at a fusion site or disc implant interface. The parameters of micro-motion would then be evaluated. In one embodiment, the computer can produce a work flow to correct the issue based on the measurement data. In general, the relative motion and the angular changes between implantable devices 24 and 26 would be monitored. The patient activities can be modified or the segment stabilized with micro invasive approaches that are minimally invasive if abnormal motion at the surrounding segments is detected. The same technology can be used in a cage or an artificial disc motion implant.

Surgical system 10 disclosed herein below will call out components from FIGS. 1-9. Surgical system 10 is configured to be used in an operating room to install at least one prosthetic component. Surgical system 10 comprises a drill, a surgical navigation system 30, and an implantable device 24. Surgical navigation system 30 can be called navigation system 30. In one embodiment, the drill is configured to drill at least one hole in a bone of the musculoskeletal system through an open wound that supports the installation of the at least one prosthetic component. Note that in the example, no wound is made to install the implantable device 24. The wound exists due to the implant surgery. Implantable device 24 has at least one inertial measurement unit (IMU) 80. Implantable device 24 has a hermetically sealed enclosure 40 and at least one anchor extending from enclosure 40. In the example, an anchor 42 and an anchor 44 extends from enclosure 40 of implantable device 24. Anchors 42 and 44 include a plurality of barbs or threads configured to resist pull out and reduces stress risers in bone adjacent to holes 34. The drill is configured to drill two holes 34 in tibia 20. Anchors 42 and 44 of implantable device 24 are configured to be inserted in holes 34 after tracking device 18 is removed from tibia 20. Holes 34 can be filled with adhesive to strengthen the bone adjacent to holes 34 and then inserting anchors 42 and 44 to retain implantable device 24. In one embodiment, anchors 42 and 44 can be porous or have openings to couple to bone. In one embodiment, holes 34 can be filled with bone growth hormone to support bone growth through anchors 42 and 44 and reduce stress risers in bone adjacent to holes 34. Anchors 42 and 44 are configured to retain implantable device 24 and reduce stress risers from holes 34 in tibia 20. In one embodiment, anchors 42 and 44 permanently fixes implantable device 24 to tibia 20. Implantable device 24 is configured to measure bone position, bone movement, bone orientation or increase bone strength in holes 34.

Implantable device 24 further includes a printed circuit board 52, electronic circuitry 54, and enclosure 40. Electronic circuitry 54 couples to printed circuit board 52 to form an electronic system configured to control a measurement process and transmit measurement data. Enclosure 40 of implantable device 24 houses the electronic circuitry 54 and printed circuit board 52. In one embodiment, enclosure 40 is hermetically sealed to isolate a cavity 50 from an external environment. Implantable device 24 is configured to receive energy from an external power source 28. In one embodiment, external power source 28 is external to a body of the patient. External power source 28 is configured to couple to implantable device 24 to couple energy to implantable device 24 for operation. Implantable device 24 can further include one or more sensors coupled to electronic circuitry 54. In one embodiment, implantable device 24 supports infection detection, pain mitigation rehabilitation, and long-term monitoring of the at least one prosthetic component.

Surgical navigation system 30 comprises a computer 12, a tracking device 14, a tracking device 16, and a tracking device 18. Tracking device 14 is configured to couple to holes 32 drilled in femur 22. Similarly, tracking device 18 is configured to couple to holes 34 drilled in tibia 20. In one embodiment, holes 32 and 34 are drilled in areas of femur 22 and tibia 20 that are exposed by the open wound made by the surgeon to install one or more prosthetic components. Surgical navigation system 30 is configured to monitor and measure movement, position, or orientation of femur 22 and tibia 20. Surgical navigation system 30 supports installation of at least one prosthetic component. In one embodiment, navigation is configured to support alignment of femur 22 to tibia 20. Surgical navigation system 30 is configured to register a location of holes 32 and 34 drilled to mount tracking device 14 and tracking device 18. The location of holes 32 and 34 can be provide to implantable devices 24 and 26 or to a computer to establish a geometric registration to femur 22 and tibia 20. The computer is configured to couple to implantable devices 24 and 26 for receiving measurement data.

Surgical system 10 supports the installation of at least one prosthetic component in a joint of the musculoskeletal system. In the example, surgical system 10 is configured to support a total knee arthroplasty comprising femoral prosthetic component 90, an insert 92, and a tibial prosthetic component 94. The surgeon creates a wound to expose a portion of a femur 22 and a portion of tibia 20 for access to the knee joint. Surgical system 10 comprises a surgical navigation system 30, implantable device, 26, implantable device 24, a drill, femoral prosthetic component 90, insert 92, and tibial prosthetic component 94. Navigation system 30 is configured to couple to the exposed femur 22 and tibia 20 through the open wound created by the surgeon to install the prosthetic knee joint. Holes 32 and holes 34 are respectively drilled in femur 22 and tibia 20 in areas exposed by the wound. Tracking device 14 is configured to couple to holes 32 in femur 22. Tracking device 18 is configured to couple to holes 34 in tibia 20. Surgical navigation system 30 is configured to measure movement, position, or orientation of the first bone relative to the second bone. Surgical navigation system 30 is configured to support the installation of the prosthetic knee joint comprising femoral prosthetic component 90, insert 92, and tibial prosthetic component 94. Surgical navigation system 30 is configured to register a location of holes 32 and holes 34 respectively in femur 22 and tibia 20. A geometric registration to femur 22 and tibia 20 is established by registering a position of holes 32 and holes 34.

Surgical system 10 further includes implantable device 24 and implantable device 26. Implantable devices 24 and 26 each include an IMU 80. An anchor 42 and an anchor 44 extend from enclosure 40 of implantable device 24. Anchors 42 and 44 of implantable device 24 are configured to couple within holes 34 in tibia 20 after tracking device 18 of surgical navigation system 30 is removed. Similarly, an anchor 42 and an anchor 44 extend from enclosure 40 of implantable device 26. Anchors 42 and 44 of implantable device 26 are configured to couple within holes 32 in femur 22 after tracking device 14 of surgical navigation system 30 is removed. In one embodiment, holes 32 and 34 can be filled with adhesive prior to inserting implantable devices 26 and 24. In one embodiment, implantable devices 24 and 26 have a fixed position relative to tibia 20 and femur 22. Implantable devices 24 and 26 are configured to measure movement and position of tibia 20 and femur 22 post-operatively. In one embodiment, implantable devices 24 and 26 are configured to reduce stress risers due to holes 32 and holes 34 in femur 22 and tibia 20.

Implantable devices 24 and 26 are respectively coupled to holes 34 and 32 in tibia 20 and femur 22. As mentioned, holes 32 and 34 are exposed from the wound for implanting the knee joint. Thus, implantable devices 24 and 26 can be respectively coupled to holes 34 and 32 without creating a new wound. In one embodiment, implantable devices 24 and 26 are permanently coupled to tibia 20 and femur 22. Implantable devices 24 and 26 are configured to monitor position, movement, or orientation of tibia 20 and femur 22 similar to surgical navigation system 30 post-operatively. Implantable devices 24 and 26 are configured to receive energy from at least one external power source 28. Implantable devices 24 and 26 receive energy from external power source 28 until each implantable device has sufficient power stored to perform at least one task. Implantable devices 24 and 26 can include one or more sensors 82 and the IMU 80. In one embodiment, sensors 82 and IMU 80 can be configured of implantable device 24 or implantable device 26 can be configured for infection detection, pain mitigation, rehabilitation, and long-term monitoring of the knee joint or a prosthetic component. In one embodiment, a registration process of implantable device 24 and implantable device 26 can include one or more movements of tibia 20 and femur 22 to locate positions of implantable devices 24 and 26 relative to tibia 20 and femur 22.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the claims. While the subject matter of the invention is described with specific examples of embodiments, the foregoing drawings and descriptions thereof depict only typical embodiments of the subject matter and are not therefore to be considered to be limiting of its scope, it is evident that many alternatives and variations will be apparent to those skilled in the art. Thus, the description of the invention is merely descriptive in nature and, thus, variations that do not depart from the gist of the invention are intended to be within the scope of the embodiments of the present invention. Such variations are not to be regarded as a departure from the spirit and scope of the present invention.

While the present invention has been described with reference to embodiments, it is to be understood that the invention is not limited to the disclosed embodiments. The scope of the following claims is to be accorded the broadest interpretation so as to encompass all modifications, equivalent structures and functions. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

As the claims hereinafter reflect, inventive aspects may lie in less than all features of a single foregoing disclosed embodiment. Thus, the hereinafter expressed claims are hereby expressly incorporated into this Detailed Description of the Drawings, with each claim standing on its own as a separate embodiment of an invention. Furthermore, while some embodiments described herein include some but not other features included in other embodiments, combinations of features of different embodiments are meant to be within the scope of the invention, and form different embodiments, as would be understood by those skilled in the art.

What is claimed is:

1. A surgical system comprising:

a prosthetic component configured for installation in a joint of a musculoskeletal system, wherein the joint includes an first bone and a second bone;

a navigation system configured to couple to the first bone and the second bone of the joint, wherein a first tracking device is configured to be coupled to the first bone through a hole drilled in the first bone, wherein a second tracking device is configured to be coupled to the second bone through a hole drilled in the second bone, wherein both the first tracking device and the second tracking device are configured to measure at least one of relative movement, relative position, or relative orientation of the first bone and the second bone;

a first implantable device comprising an inertial measurement unit (IMU), wherein an enclosure of the first implantable device comprises an anchor, wherein the anchor is (i) configured to be inserted in and fill the hole in the first bone and (ii) extends from the enclosure; and a second implantable device comprising an inertial measurement unit (IMU), wherein an enclosure of the second implantable device comprises an anchor, wherein the anchor of the second implantable device is configured to be inserted in and fill the hole in the second bone, and wherein the first and the second implantable device are configured to measure movement, position, or orientation of the first bone and the second bone.

2. The surgical system of claim 1, wherein the navigation system is further configured to register a location of the hole in the first bone and the hole in the second bone, wherein the location of the hole in the first bone and the location of the hole in the second bone is transmitted to the first implantable device and the second implantable device, wherein a geometric registration is based on at least the location of the hole in the first bone and the location of the hole in the second bone.

3. The surgical system of claim 1, wherein the first implantable device and the second implantable device are respectively configured to be permanently coupled to the first bone and the second bone, and wherein the first implantable device and the second implantable device are configured to monitor at least one of position, movement, or orientation of the first bone relative to the second bone.

4. The surgical system of claim 1 wherein the hole in the first bone or the hole in the second bone is filled with adhesive prior to inserting the anchor of the first implantable device or the second implantable device.

5. The surgical system of claim 1 wherein the first implantable device and the second implantable device are configured to receive energy from an external source until sufficient power is stored to perform at least one task, wherein each of the first implantable device and the second implantable device includes one or more sensors configured to generate measurement data associated with the at least one task, wherein the at least one task includes infection detection, pain mitigation, rehabilitation, or long-term monitoring of the at least one prosthetic component or the joint.

6. The surgical system of claim 1 wherein the first implantable device includes:

a printed circuit board;

electronic circuitry coupled to the printed circuit board to form an electronic system;

the electronic system configured to control a measurement process and transmit measurement data, wherein the enclosure of the first implantable device houses the electronic circuitry and printed circuit board, and wherein the enclosure is hermetically sealed; and one or more sensors coupled to the electronic circuitry.

7. The surgical system of claim 1, wherein a registration process of the first implantable device and the second implantable device includes one or more movements of the first bone and the second bone to locate positions of the first implantable device and the second implantable device relative to the first bone and the second bone.

8. A surgical system, comprising:

a first prosthetic component configured to be coupled to a knee joint;

a navigation system configured to be coupled to a first bone of the knee joint and a second bone, wherein a first device of the navigation system is configured to be coupled to a first hole drilled in the first bone, wherein a second device of the navigation system is configured to be coupled to a second hole drilled in the second bone, wherein the first device and the second device are configured to measure at least one of movement, position, or orientation of the first bone relative to the second bone intra-operatively during an insertion of the prosthetic component;

a first implantable device comprising an inertial measurement unit (IMU) and an anchor, the anchor configured to be inserted in the first hole in the first bone; and a second implantable device comprising an inertial measurement unit (IMU) and an anchor, the anchor configured to be inserted in and fill the second hole in the second bone, and wherein the first implantable device and the second implantable device are configured to measure at least one of movement, position, or orientation of the first bone and the second bone post-operatively.

9. The surgical system of claim 8, wherein the first bone and the second bone are part of the knee joint.

10. The surgical system of claim 9, further comprising:

a second prosthetic component configured to be coupled to the knee joint.

11. The surgical system of claim 10, wherein the second implantable device is configured to measure movement, position, or orientation of the second prosthetic component relative to the second implantable device.

12. The surgical system of claim 11, wherein the navigation system is further configured to measure movement, position, or orientation of the first device relative to the second device.

13. The surgical system of claim 11, further comprising:

a third prosthetic component operably coupled to both the first prosthetic component and the second prosthetic component.

14. The surgical system of claim 13, wherein the knee joint includes the first prosthetic component, the second prosthetic component, and the third prosthetic component.

15. The surgical system of claim 8, further comprising a display for displaying a position of the knee joint with cartesian coordinates and axes of rotation.

16. A surgical system, comprising:

a navigation system configured to be coupled to a first bone of the knee joint and a second bone of the knee joint, wherein a first device of the navigation system is configured to be coupled to a first hole drilled in the first bone, wherein a second device of the navigation system is configured to be coupled to a second hole drilled in the second bone, wherein the first device and the second device are configured to measure at least one of movement, position, or orientation of the first bone relative to the second bone intra-operatively during an insertion of a first prosthetic component;

a first implantable device comprising a first sensor and an anchor, the anchor configured to be inserted in and fill the first hole in the first bone; and a second implantable device comprising a second sensor and an anchor, the anchor configured to be inserted in the second hole in the second bone, and wherein the first and the second implantable device are configured to measure at least one of movement, position, or orientation of the first bone and the second bone post-operatively.

17. The surgical system of claim 16, wherein the first device is configured to measure a movement, a position, or an orientation of the first bone, wherein the first device is configured to communicate the measurement of at least one of the movement, the position, or the orientation of the first bone to the navigation system.

18. The surgical system of claim 17, wherein the second device is configured to measure at least one of a movement, a position, or an orientation of the second bone, wherein the second device is configured to communicate the measurement of the movement, the position, or the orientation of the second bone to the navigation system.

19. The surgical system of claim 16, further comprising:

a second prosthetic component coupled to the first prosthetic component.

20. The surgical system of claim 16, wherein the first sensor is an optical device.

21. The surgical system of claim 16, wherein the first sensor is an acoustical ranging device.

* * * * *